United States Patent [19]

Page et al.

[11] Patent Number: 5,147,788
[45] Date of Patent: Sep. 15, 1992

[54] BACULOVIRUS VECTORS AND METHODS OF USE

[75] Inventors: Martin J. Page; Brian C. Rodgers, both of Beckenham, United Kingdom

[73] Assignee: Burroughs Wellcome Co., Research Triangle, N.C.

[21] Appl. No.: 622,177

[22] Filed: Dec. 3, 1990

Related U.S. Application Data

[63] Continuation of Ser. No. 256,496, Oct. 12, 1988, abandoned.

[30] Foreign Application Priority Data

May 6, 1988 [GB] United Kingdom ............... 8810808

[51] Int. Cl.$^5$ ...................... C12N 15/86; C12N 15/00; C12P 21/02
[52] U.S. Cl. ................................. 435/69.1; 435/69.51; 435/69.3; 435/69.7; 435/320.1; 435/172.3; 935/60; 935/34
[58] Field of Search ................ 435/69.1, 320.1, 69.51, 435/69.3, 69.7, 172.3

[56] References Cited

U.S. PATENT DOCUMENTS 4,745,051  5/1988  Smith ................................ 435/69.1

FOREIGN PATENT DOCUMENTS

| AU-B- | | |
|---|---|---|
| 28717/84 | 11/1984 | Australia . |
| 0155476 | 9/1985 | European Pat. Off. . |
| 0228036 | 7/1987 | European Pat. Off. . |
| 0260090 | 3/1988 | European Pat. Off. . |
| 208259 | 5/1984 | New Zealand . |
| 88/02030 | 3/1988 | PCT Int'l Appl. . |

OTHER PUBLICATIONS

M J Page, Nucleic Acids Research, vol. 17 p. 454, (1989).
Luckow & Summers, Virology 167 pp. 56-71, (1988).
Enea V. et al 1984 Science 225: 628-630.
Nishi T. et al 1985 J. Biochem 97: 153-159.
Hermiston T. W. et al 1987 Oct. J. Virol. 61(10) 3214-3221.
Luckow V. A. and Summers M.D. Jan., 1988 Bio/Technology 6: 47-55.
Smith G. E. Mol. Cell Biol Dec. 1983 3(12) 2156-2165.
Hope I A et al Jan. 25, 1985 Nucl Acids Research 13(2) 369-379.
Kuroda K. et al 1986 EMBO J. 5(6) 1359-1365.
McCutchan T F et al 1985 Science 230: 1381-1383.
Y. Matsuura, et al., J. Gen. Virol. (1987), 68, pp. 1233-1250. Baculovirus Expression Vectors: the Requirements for High Level Expression of Proteins, Including Glycoproteins.
Table of Contents, vol. 15, No. 24, Dec. 23, 1987, Nucleic Acids Research, pp. 10233-10249.

Primary Examiner—Richard A. Schwartz
Assistant Examiner—S. L. Nolan
Attorney, Agent, or Firm—Donald Brown; Lawrence Neilsen

[57] ABSTRACT

A baculovirus transfer vector incorporates a restriction site into which a foreign gene may be cloned a short distance downstream of the N-terminus of the polyhedrin gene body and the natural ATG translation start codon for the polyhedrin gene is not provided such that the N-terminal polyhedrin coding sequence prior to the restriction site is retained but not capable of being translated.

22 Claims, 5 Drawing Sheets

BACULOVIRUS VECTORS AND METHODS OF USE

This is a continuation of copending application Ser. No. 07/256,496 filed on Oct. 12, 1988, now abandoned.

This invention relates to baculovirus transfer vectors and to their use.

The baculovirus vector system has been used to express both procaryotic and eucaryotic genes. The expression of these genes is controlled by the polyhedrin promoter of a baculovirus, in particular of *Autographa californica* nuclear polyhedrosis virus (AcNPV). The foreign genes are expressed in insect cells in culture which are infected with recombinant baculovirus incorporating the foreign gene.

In order to obtain a recombinant baculovirus, a baculovirus transfer vector is used. This vector includes the polyhedrin promoter. Baculovirus DNA flanking the polyhedrin gene is provided. The rest of the vector is typically made up of DNA from a bacterial plasmid. A foreign gene is inserted into the transfer vector downstream of the polyhedrin promoter such that its expression is controlled by this promoter.

The transfer vector containing the foreign gene and a baculovirus then co-transfect insect cells susceptible to baculovirus infection. Typically *Spodoptera frugiperda* cell cultures are utilised. Homologous recombination then occurs involving the viral DNA in the transfer vector upstream and downstream of the foreign gene and the corresponding DNA of the baculovirus. The foreign gene and its polyhedrin promoter is therefore transferred to the baculovirus. The recombinant baculovirus is cultured to express the foreign gene.

There are two types of baculovirus transfer vectors. First, there are transfer vectors which include a restriction site into which a foreign gene may be cloned downstream of the polyhedrin ATG start codon for translation. Such transfer vectors result in fusion proteins in which the product of the foreign gene is fused to a N-terminal portion of the polyhedrin peptide.

Second, there are transfer vectors which the 5' untranslated leader of the polyhedrin gene ends before the natural ATG translation start codon for polyhedrin and a restriction site is then provided. Such a transfer vector is pAc373 in which the 5' untranslated leader ends 8 bases upstream of the natural polyhedrin ATG start codon. Genes cloned into the restriction site are expressed as mature proteins if they contain an ATG followed by an open reading frame coding for the desired product.

According to the present invention, there is provided a baculovirus transfer vector which incorporates a restriction site into which a foreign gene may be cloned a short distance downstream of the N-terminus of the polyhedrin gene body and in which the natural ATG translation start codon for the polyhedrin gene is not provided such that the N-terminal polyhedrin coding sequence prior to the restriction site is retained but not capable of being translated.

In the baculovirus transfer vector of the invention, therefore, a non-coding sequence is provided in place of the natural ATG translation start codon for polyhedrin. The N-terminal body of the polyhedrin coding sequence is not now translated but serves the role of an extended leader sequence. A useful alternative baculovirus transfer vector is therefore provided which retains DNA sequence information, which may be beneficial for expression of mature proteins, attributable to the N-terminal body of the polyhedrin coding sequence. We have found that a foreign gene provided with an ATG translation start codon can be expressed in high yields when cloned into the restriction site of the transfer vector. Advantageously, the product expressed is not in the form of a fusion protein incorporating residual N-terminal polyhedrin amino acids.

A restriction site is provided in the baculovirus transfer vector downstream of and within a short distance of the N-terminus of the polyhedrin gene body. The restriction site may be provided after the first 24 to 50 bases, for example after the first 27 to 39 bases, of the N-terminal region of the polyhedrin gene. More preferably, the site is provided after about the first 33 bases. A BamHl linker may be inserted, for example.

The natural ATG polyhedrin translation start codon is changed to non-coding information. The start codon can be replaced by any other triplet of nucleotides. Preferably there is a single base change in the natural ATG start codon, more preferably in the third base of the codon. ATG may therefore be changed to ATA, ATT or especially ATC. As a result, expression of the N-terminal body of the polyhedrin gene will not occur but instead commence at the first ATG encountered within a sequence introduced at the restriction site. In this way, DNA sequence information present within the N-terminal body of the polyhedrin gene itself may contribute to high expression of a foreign gene.

A preferred transfer vector is pAc36C. This was constructed from the transfer vector pAc360 (Summers and Smith, 1987, "A Manual of methods for Baculovirus vectors and Insect cell culture procedure") by site directed mutagenesis in which the ATG translation start codon for polyhedrin within pAc360 was converted to ATC.

pAc360
TATAAT ATG CCG GAT TAT TCA TAC CGT CCC ACC ATC GGG (Bam H1)
Translated N-terminal body of polyhedrin gene pAc36c
TATAAT ATC CCG GAT TAT TCA TAC CGT CCC ACC ATC GGG (Bam H1).

A baculovirus transfer vector according to the invention may be constructed by mutating to non-coding sequence the natural ATG translation start codon for polyhedrin of a baculovirus transfer vector in which a restriction site into which a foreign gene may be cloned is provided a short distance downstream of the N-terminus of the polyhedrin gene body. This is typically achieved by site-directed mutagenesis. A mutation, preferably a point mutation, can be introduced using a synthetic oligonucleotide comprising the desired sequence.

A recombinant baculovirus incorporating a foreign gene is derived from the transfer vector by:

(a) cloning a foreign gene provided with a translation start codon into the baculovirus transfer vector at the restriction site provided; and (b) co-transfecting insect cells susceptible to baculovirus infection with the recombinant baculovirus transfer vector from step (a) and with intact wild type baculovirus DNA.

The foreign gene is cloned into the baculovirus transfer vector in step (a) so that it is under the transcriptional control of the polyhedrin promoter. Typically cells of the *Spodoptera frugiperda* insect cell line are co-transfected in step (b). Following homologous recombination, the foreign gene and flanking portions of viral DNA are transferred to the baculovirus AcNPV. Recombinant baculovirus are screened for, for example by plaque assay, and purified.

In order to obtain the product encoded by the foreign gene, cells susceptible to baculovirus infection are infected with the recombinant baculovirus and cultured. Again, cells of the *Spodoptera frugiperda* insect cell line are typically utilised. As the foreign gene is under the transcriptional control of the polyhedrin promoter, high yields of the gene product may be achieved.

Any foreign gene, procaryotic or eucaryotic, may be expressed in this way. For example, an intracellular mature form of human gamma-interferon or of cytomegalovirus immediate early protein can be expressed. We have also successfully expressed chaemeric proteins consisting essentially of:

(i) at the N-terminus of the chaemeric protein, a signal sequence of the precursor to the major merozoite surface antigens (PMMSA) of *P. falciparum;*

(ii) optionally, at least one epitope of the circumsporozoite protein (CSP) of *P. falciparum;* and (iii) a C-terminal fragment of the PMMSA of *P. falciparum* with or without the C-terminal anchor sequence.

Short linking sequences of up to 30 amino acid residues may be provided between these components. These chimaeric proteins, potentially useful as vaccines, were expressed with the correct conformation. The CSP epitope(s) (ii) preferably consisted of from 3 to 50, for example from 16 to 30, repeats of the tetrapeptide sequence Asn-Ala-Asn-Pro.

The following Examples illustrate the invention. In the accompanying drawings:

FIG. 1 shows the PMMSA and CSP genes, the portions of them employed in the Examples and synthetic linkers employed in the Examples. The following restriction sites are marked: A-AluI, B-BamHl, H-HindIII, P-PstI, T-TthIII and X-XhoII. A represent the anchor sequence. S represents the signal sequence.

EXAMPLE 1

Construction of Transfer Vector pAc36C

The transfer vector pAc36C was derived from pAc360 (Summers and Smith, 1987, "A Manual of methods for baculovirus vectors and insect cell culture procedures") by site directed mutatgenesis using kits obtained from Anglian Biotech and Amersham International. An 852 bp cDNA for human gamma interferon was subcloned as a BamHl fragment into the BamHl site of pAc360. From this a lkb DraI fragment which extends from about 700 bp upstream of the polyhedrin ATG translation start codon to 300 bp inside the 5' end of the gamma interferon cDNA insert was subcloned into the SmaI site of M13K19 (Anglian Biotech). The RF form of the construct was used to confirm the ligation and single strand template was derived and mutated with the 19 mer:

GAATAATCCGG$\underline{G}$ATATTTA.

The underlined G had the effect of converting the ATG of the polyhedrin translation codon to ATC. The mutation was confirmed by DNA sequencing and a 136 bp EcoRV-BamHl fragment encompassing the mutation was used to replace the same fragment in pAc360 with the mutagenised fragment to derive pAc36C.

EXAMPLE 2

Construction of Recombinant Transfer Vectors derived from pAc36C

Figure 1:
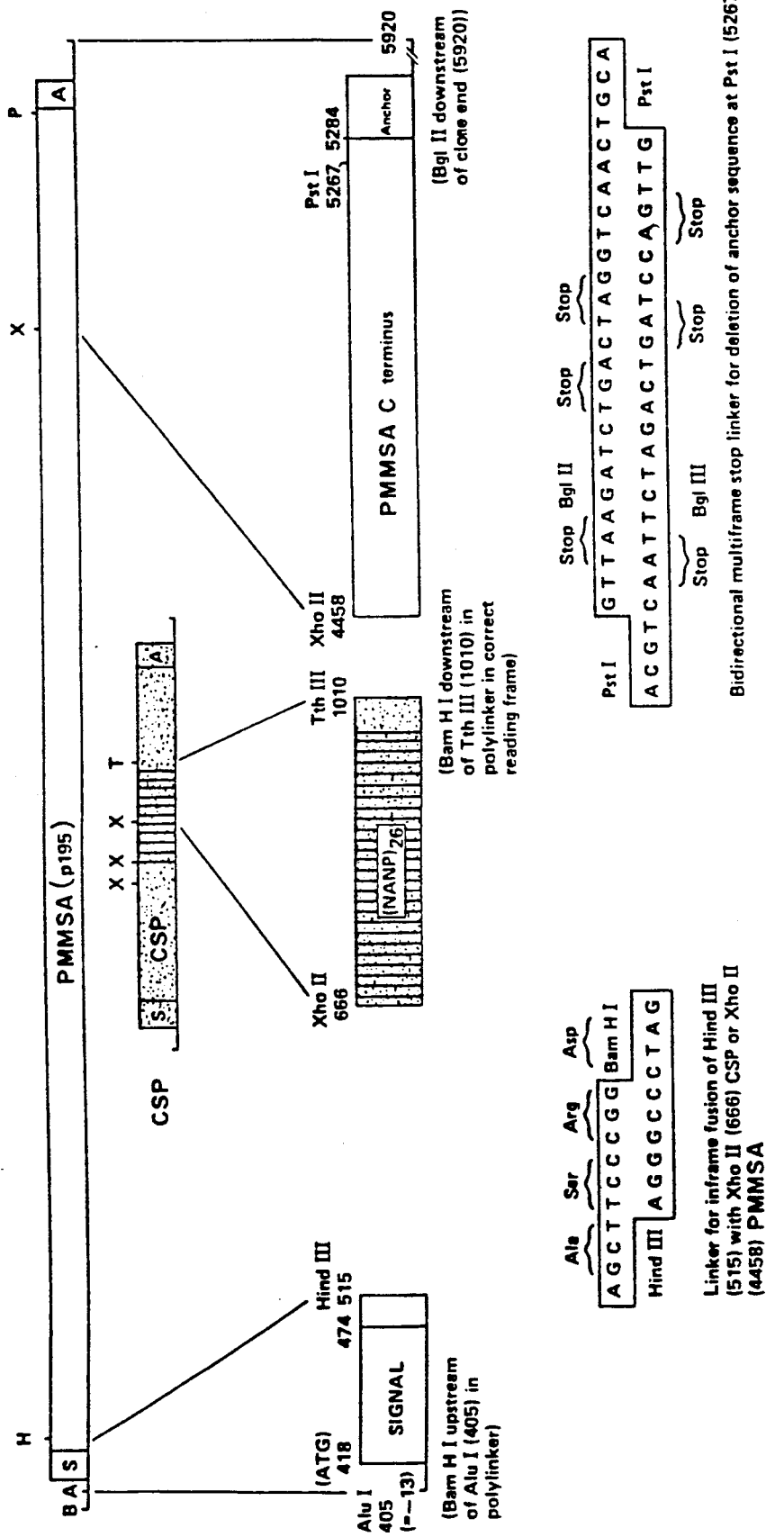
Figure 2:
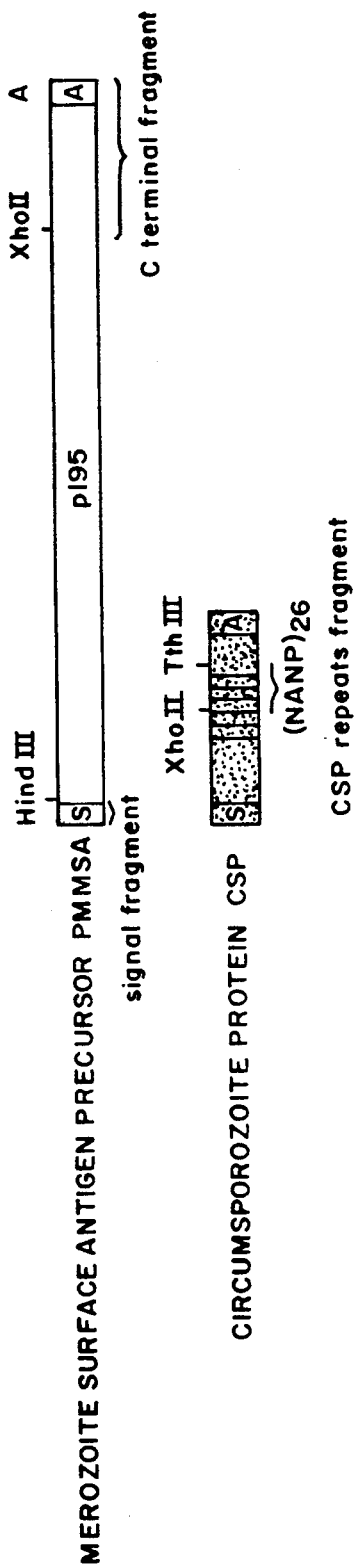
FIG. 2 shows the structural genes employed in obtaining the recombinant transfer vectors and each recombinant baculovirus Examples 2 and 3.

The recombinant transfer vector pS42 was constructed in three steps. Firstly, pAc36C42 was made by cloning the 1.46 kb XhoII/BglII fragment of pPfc1028 (Holder et al, Nature, 317, 270–273, 1985) into the BamHl site of pAc36C. Secondly, a 120 base pair fragment from the N terminus of PMMSA was excised from pPfc1017 (Holder et al, 1985) by HindIII and AluI digestion. This fragment contains a short 12 base pair leader, a translation initiation codon, the 18 amino acid PMMSA signal peptide, and 15 additional amino acids from the N terminus of PMMSA. This was subcloned into pUC9 digested with HindIII and HindII and was then excised as a HindIII/BamHl fragment, the BamHl site being provided by the pUC9 polylinker. In the final cloning step this 120 base pair BamHl/HindIII fragment was cloned into the unique BamHI site of p36-C42 with a synthetic 10 base pair HindIII/BamHl linker which also placed the fusion in the correct reading frame. The linker is shown in FIG. 1. The gene incorporated in pS42 under the control of the polyhedrin promoter is shown in FIG. 2.

A second recombinant transfer vector pSC$_{26}$42 was constructed by ligation of three fragments: the 1.15 kb BamHl/PstI fragment used for construction of pPC$_{26}$42, a 2.2 kb XhoI/BamHl fragment and a 7 kb XhoI/PstI fragment excised from pS42 by PstI and XhoI digestion and partial BamHl digestion pPC$_{26}$42 was constructed as follows:

(i) a recombinant transfer vector pP42 was constructed by converting the HindIII site of pPfc1028 to BglII by digestion with HindIII, blunting with Klenow polymerase and ligation of BglII linkers. Digestion with XhoII gave a 1.46 kb XhoII/BglII fragment which was cloned into the unique BamHI site of pAc360 to give an in frame fusion of the first 10 amino acids of polyhedrin with the C terminal 293 amino acids of PMMSA. The gene incorporated in pP42 is shown in FIG. 2. This gene is under the control of the polyhedrin promoter.

(ii) To construct pPC$_{26}$42, 26 copies of the CSP tetrapeptide repeat were cloned at the polyhedrin/FMMSA junction of pP42 by replacement of the small BamHl/PstI fragment of pP42 with a 1.15 kb fragment obtained by PstI digestion and partial BamHI digestion of the bacterial expression vector p750/CSPa/P195 (EP-A-0250261).

Two further recombinant transfer vectors were constructed with a synthetic oligonucleotide to prevent expression of the C-terminal anchor sequence of PMMSA. These anchor sequence-deleted constructs pS42ΔA and pSC$_{26}$42ΔA, were made by the construction of a synthetic 26 base pair PstI linker containing bidirectional translation stop codons in all reading frames. This linker is shown in FIG. 1. The linker was cloned into the unique PstI site of both pS42 and pSC$_{26}$42 just upstream of the putative membrane anchor sequences. The genes in pS42ΔA and pSC$_{26}$42ΔA under the control of the polyhedrin promoter are shown in FIG. 2.

All cloning steps were carried out using standard procedures (Maniatis et al, "Molecular Cloning: A Laboratory Manual", N.Y.: Cold Spring Harbor Laboratory, 1982). Correct ligation and orientation of the fragments was analysed by fine restriction enzyme mapping. Plasmids used for transfection were purified from bacterial cultures by caesium chloride gradient centrifugation.

EXAMPLE 3

Generation of Recombinant Viruses

*Spodoptera frugiperda* (Sf) cells (IPLB Sf 21) (Vaughn et al, In vitro, 13, 213-217, 1977) were grown in suspension cultures at 22° C. or 27° C. in TC100 medium (Flow Labs) supplemented with 10% foetal bovine serum (Gibco). AcNPV (strain E2) was propagated in Sf cells grown at 27° C. in suspension cultures. Recombinant viruses containing the *P. falciparum* gene sequences shown in FIG. 2 were generated by cotransfection of a 20:1 molar ratio of the recombinant transfer vectors prepared in Example 2 with AcNPV DNA purified from extracellular virus (ECV) cultures in Sf cells. The method for purification of AcNPV DNA was as described (Summers and Smith, 1987) except that cultures were infected at 1 pfu per cell and harvested after 6 days and the sucrose gradient step was omitted. Cotransfection was as described (Summers and Smith, 1987, method 1).

The resultant ECV was screened for recombinants by plaque assay three days after transfection. Plaque assays were carried out essentially as described (Brown and Faulkener, J. Gen. Virol., 36, 361-364, 1977) using serial dilutions of the transfection culture supernatant. Following neutral red staining potential recombinant plaques were selected visually for the absence of polyhedra, picked into 0.5 ml of culture medium and purified by repeated plaque assay. Recombinant viruses were scaled up from plaques or monolayer culture and grown on a large scale in suspension or roller bottle cultures. The recombinant virus obtained are shown in FIG. 2.

EXAMPLE 4

Analysis of Proteins from Cells infected with the Recombinant Viruses

Potential recombinant viruses generated in Example 3 were assayed initially for expression of *P. falciparum* sequences by dot blot assay. Polyhedrin negative plaques were picked into 0.5 ml of culture medium and allowed to diffuse for at least one hour. 100 μl of this was used to infect $2 \times 10^5$ cells in a 35 mm petri dish, and incubated at room temperature for one hour. The inoculum was then replaced with 1 ml of culture medium and the plates were then incubated for three to four days at 27° C. Cells were then washed once in phosphate buffered saline (PBS) and harvested by centrifugation. Cell pellets were lysed in 1% sodium dodecyl sulphate (SDS) and applied to nitrocellulose filters under vacuum using a dot blot apparatus.

For detection of secreted proteins, the medium was replaced with 0.5 ml of serum free medium three days post infection and 100μl was applied directly to the nitrocellulose after twenty four hours incubation at 27° C. Filters were probed with a rabbit polyclonal antiserum raised against native PMMSA followed by an alkaline phosphatase conjugated anti-rabbit IgG antibody (Sigma). Antibody binding was detected with a chromogenic substrate.

For more detailed analysis of cell lysates and culture supernatants, SDS/polyacrylamide gel electrophoresis (PAGE) under reducing and non-reducing conditions was used followed by staining with Coomassie blue or Western blotting using a range of specific antisera and monoclonals. These were two polyclonal rabbit antisera, one, (Pas PMMSA), raised against native PMMSA and another, (Pas NANP), raised against a synthetic petpide corresponding to the tetrapeptide repeat (NANP) of CSP, linked to bovine serum albumen, and several mouse monoclonal antibodies raised against native PMMSA and recognising conformational reduction sensitive epitopes in the C terminus (Mab 111.4, Mab 117.2 and Mab 111.2).

Dot blot analysis indicated that antigenic products recognised by Pas PMMSA were expressed by both recombinant viruses vS42 and vSC$_{26}$42 in infected Sf cells. Cells infected with vS42 produced a novel protein which was not visible on Coomassie blue stained gels, but was readily deteoted on Western blots as a 36-38kd protein appearing as three distinct bands recognised by Pas PMMSA and more significantly by Mab 111.4 under non reducing conditions. vSC$_{26}$42 infected cells also produced a novel protein of around 50kd, also migrating as three closely spaced bands. The 50kd protein was clearly visible by Coomassie staining at levels of expression similar to that seen for the product of vP42, and was strongly recognised by Pas PMMSA, Pas NANP, Mab 111.4, Mab 111.2 and Mab 117.2. The monoclonals as expected recognised the protein only under non reducing conditions and the recognition of both by Pas PMMSA was stronger with the non-reduced protein. Both recombinant products were insoluble in Nonidet P40 (NP40), Rennex (RX) and deoxycholate (DOC) but were soluble in cetyl trimethylammonium bromide (CTAB) and SDS. The yields of the fusion proteins were <1ug/ml and 10-20 ug/ml for vS42 and vSC$_{26}$42 respectively.

For both recombinant viruses vS42ΔA and vSC$_{26}$42ΔA, dot blot analyses showed that both the cells and the culture supernatant from infected cultures contained antigenic products recognised by Pas FMMSA. Analysis by SDS/PAGE revealed novel proteins of 36-38kd for vS42ΔA and around 50kd for vSC$_{26}$42ΔA expressed at levels that were easily visible four days post infection in Coomasie blue stained gels in the cell lysate (approximately 1-2μg in $1 \times 10^5$ cells) and also in the culture supernatant at similar levels.

Both the secreted and non-secreted forms of the recombinant proteins exhibited the multiple banding in PAGE as seen for the products expressed by vS42 and vSC$_{26}$42 and both were recognised by Pas PMMSA, Mab 111.4, Mab 111.2 and Mab 117.2, and the 50kd product of vSC$_{26}$42ΔA was also recognised by Pas NANP. The recognition by the Mabs was only seen under non-reducing conditions and the recognition by Pas PMMSA was enhanced in the non-reduced state. Both recombinant products were found in the soluble fraction of the cell extract and the secreted forms were completely soluble. The yields of the fusion proteins were 7.5 ug/ml and 10 ug/ml for vS42ΔA and vSC$_{26}$42ΔA respectively.

EXAMPLE 5

Expression of the Major Immediate Early (IE) gene of Human Cytomegalovirus (HCMV) in different baculovirus vectors The major immediate early gene of HCMV encodes a spliced molecule of 1736 nucleotides, comprised of 4 exons and yields a protein of 72-76K molecular weight by SDS-PAGE. Immediate early cDNA cloned in pUC9 (Akrigg et al, 1985, Virus Research, 2 107-121) was cut with Bam HI to release a fragment containing all of the coding sequence plus about 145bp of 5' untranslated leader sequence and 90bp of 3' untranslated sequence. This fragment was gel purified and cloned into Bam HI digested, phosphatased DNA of the baculovirus transfer vectors pAc373 and pAc36C.

Baculovirus recombinants were generated by co-transfection of plasmid and wild type AcNPV DNA into *Spodoptera frugiperda* cells. Recombinant baculoviruses arising by homologous recombinant were isolated by visual screening for inclusion negative plaques, and subsequently twice plaque purified.

Comparative expression levels were analysed by $^{35}$S-methionine labelling, SDS-PAGE, Western Blot and ELISA.

i) $^{35}$S-methionine labelling : *Spodoptera frugiperda* cells (2×10$^5$ cells/3 cm dish) were infected at an m.o.i. (multiplicity of infection) of 2 and incubated at 28° C. After 24 hours, cells were rinsed 2× in PBS and labelled for 1 hour in methionine free TC100 containing 20 uCi/ml $^{35}$S-methionine. After labelling cells were washed 3 × in total cell lysates analysed by SDS-PAGE (10$^6$ cells/track) and autoradiographs.

Figure 3:
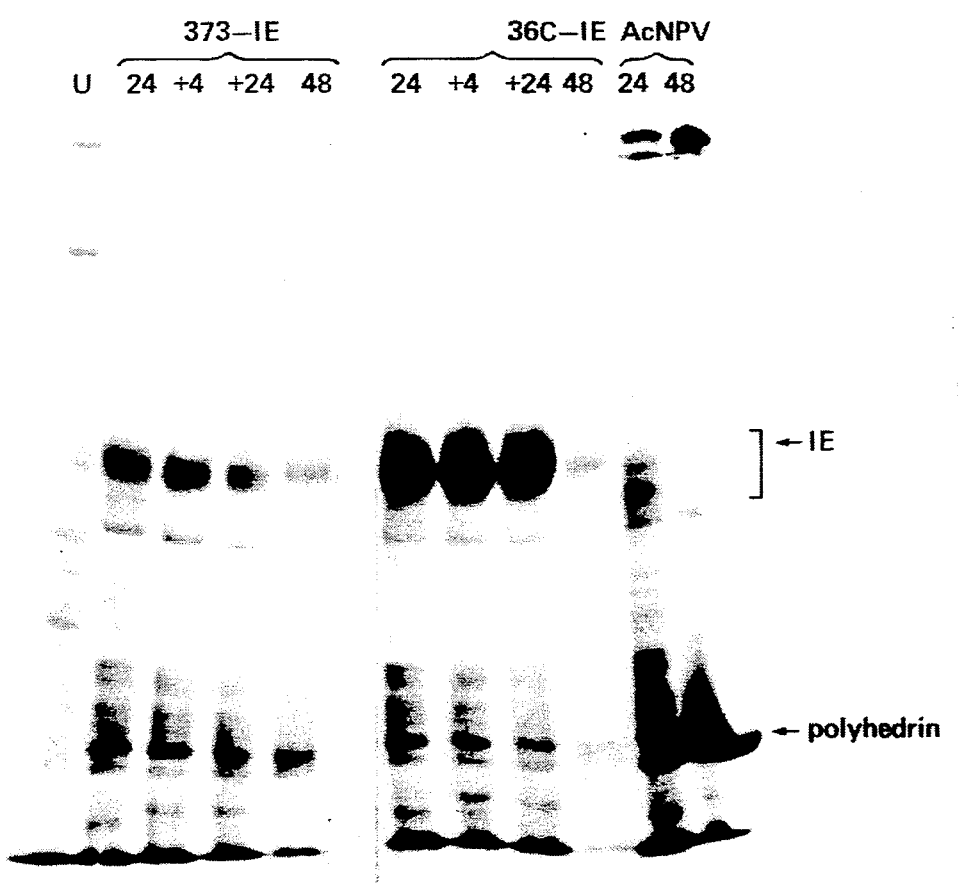
FIG. 3 shows the autoradiographs produced by $^{35}$S-methionine labelling in Example 5.

The results are shown in FIG. 3. In FIG. 3 the time points 24, +4 and +24 refer to an initial 24 hr pulse with $^{35}$S-methionine followed by 4 hr and 24 hr chase with unlabelled methionine. The time point 48 refers to a 48 hour pulse with $^{35}$S-methionine. U denotes uninfected cells.

Densitometric analysis shows the levels of methionine incorporation into recombinant product 4-5 fold greater with pAc36C (36C-IE) than with pAc373 (373-IE).

Figure 4:
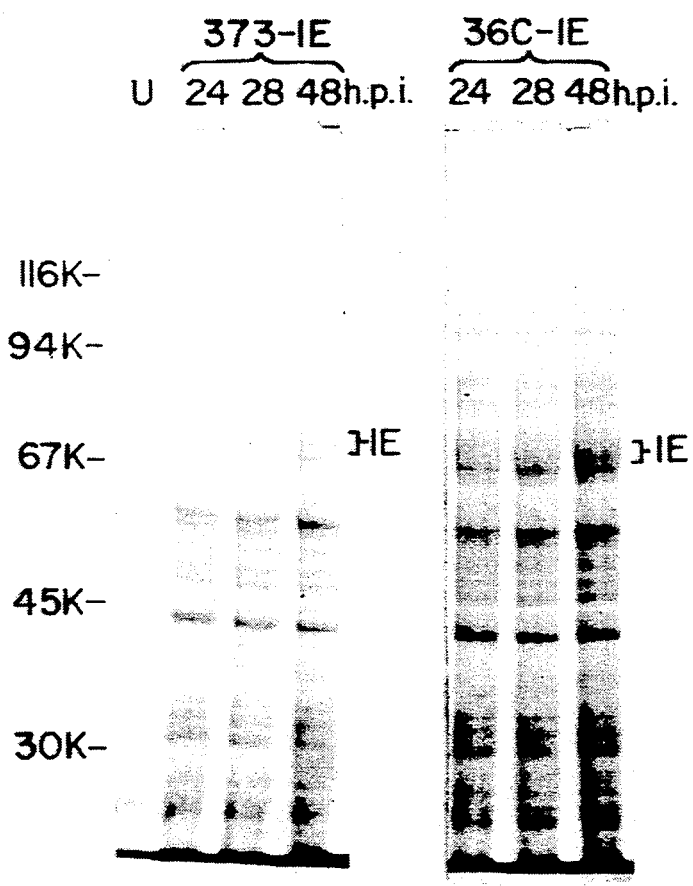
FIG. 4 shows the results of Coomassie Blue staining in Example 5.

(ii) SDS-PAGE/Coomassie Blue staining: The gel from (i) was also stained for total protein using Coomassie Blue. The results are shown in FIG. 4. As can be seen the amount of recombinant protein in the pAc36C track (36C-IE) is much higher than that in the pAc373 track (373-IE).

EXAMPLE 6

Expression of a mature intracellular form of human gamma interferon

An 852 bp AvaII-NcoI fragment was excised from pIFNγ -G4 (Nishi et al, J. Biochem. 97, 153-159, 1985) and both ends were modified with BamHI linkers. This fragment was subcloned into the unique BamHI site of pAc36C to generate pAc36C-11. From this, the entire gamma interferon cDNA was excised as a 2.74kb Sal 1-Hind III fragment and cloned into the homologous sites in the polylinker of the RF M13mp18. The 2.74kb Sal 1-Hind III sites were from the Sal 1 site approximately 820 bp upstream of the mutated ATG to ATC translation initiation codon for the polyhedrin gene to the Hind III site approximately 500bp downstream of the translation termination codon for the polyhedrin gene. The recombinant M13 clone was used to generate single strand template. This was annealed to a 33mer oligonucleotide having the sequence:

TACATATGGGTCCTGCATCCCGATGGTG-GGACG

This oligonucleotide was used to precisely fuse the 5' polyhedrin sequence of pAc36C to an ATG translation initiation codon followed by the sequence for the mature non-secreted form of human gamma interferon. This is illustrated below, with the 33 mer deletion oligonucloeotide underlined:

Polyhedrin N terminus of polyhedrin gene body
leader                         now as extended leader ACCTATAAAT ATCCCGGATTATTCATAC<u>CGTCCCACCATCGGG</u>

Mature form of
gamma interferon

<u>ATG CAG GAC CCA TAT GTA</u>

The mutagenesis kit marketed by Amersham International was used to carry out the deletion mutagenesis. Recombinant M13 plaques were identified by hybridising with the 33mer oligonucleotide which had been kinased with [$^{32}$P]-γ-ATP. Positive plaques were picked, plaque purified and used to generate single strand template for DNA sequencing to confirm the correct deletion had occurred. The RF form of a positive clone was used to excise a 135bp EcoRV-Nde I fragment encompassing the deletion. This was subsequently used in a 3 fragment ligation consisting of the large EcoRV-BamHI fragment of pAc373, the 135bp EcoRV-Nde I fragment described above and a 585bp Nde 1-Bam HI fragment reconstituting the remainder of the gamma interferon gene.

Figure 5:
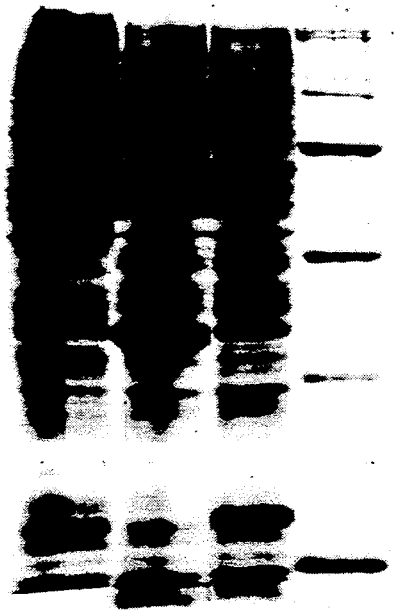
FIG. 5 shows the results of Coomassie Blue staining in Example 6.

The recombinant transfer vector thus generated (called p181) was used to generate a recombinant AcNPV as outlined in Example 3. Following infection of Sf cells at an m.o.i. of 5 pfu per cell, the cells were harvested 48 hrs post-infection, washed in PBS buffer, lysed, and run on a SDS-polyacrylamide gel, then stained with Coomassie blue. The stained tracks of the gel are shown in FIG. 5 where track 1: uninfected cells; track 2: cells infected with wild type AcNPV; track 3: cells infected with recombinant AcNPV derived from p181; and track 4: protein molecular weight markers. Densitometry scanning gave the intracellular human gamma interferon band as 14% of the total cell protein in these cells.

We claim:

1. A baculovirus transfer vector comprising the following elements operably linked 5' to 3';
   (A) a first flanking sequence composed of baculovirus DNA;
   (B) a polyhedrin promoter;
   (C) in place of the natural ATG translation start codon for the polyhedrin coding sequence, another triplet of nucleotides;
   (D) the next 21 to 47 bases of the N-terminal region of the polyhedrin coding sequence, which are thereby retained but not capable of being translated;
   (E) immediately thereafter, a restriction site into which a foreign gene may be cloned; and
   (F) a second flanking sequence composed of baculovirus DNA.

2. A vector according to claim 1, wherein the restriction site is provided after the first 27 to 39 bases of the N-terminal region of the polyhedrin gene inclusive of the triplet of nucleotides provided in place of the natural polyhedrin ATG translation start codon.

3. A vector according to claim 2, wherein the restriction site is provided after the first 33 bases inclusive of the triplet of nucleotides provided in place of the natural polyhedrin ATG translation start codon.

4. A vector according to claim 1, wherein the restriction site is a BamHl site.

5. A vector according to claim 1, wherein there is a single base change in the third base of the natural ATG translation start codon for the polyhedrin gene.

6. A vector according to claim 5, wherein the said ATG codon has been changed to ATC.

7. A process for the preparation of a recombinant baculovirus incorporating a foreign gene, which process comprises:
   (a) cloning a foreign gene provided with a translation start codon into a baculovirus transfer vector comprising the following elements operably linked 5' to 3';
   (A) a first flanking sequence composed of baculovirus DNA;
   (B) a polyhedrin promoter;
   (C) in place of the natural ATG translation start codon for the polyhedrin coding sequence, another triplet of nucleotides;
   (D) the next 21 to 47 bases of the N-terminal region of the polyhedrin coding sequence, which are thereby retained but not capable of being translated;
   (E) immediately thereafter, a restriction site into which a foreign gene may be cloned; and
   (F) a second flanking sequence composed of baculovirus DNA, and
   (G) co-transfecting insect cells susceptible to baculovirus infection with both the recombinant baculovirus transfer vector formed in step (a) and intact wild type baculovirus DNA.

8. A vector according to claim 7, wherein the restriction site is provided after the first 27 to 39 bases of the N-terminal region of the polyhedrin gene inclusive of the triplet of nucleotides provided in place of the natural polyhedrin ATG translation start codon.

9. A vector according to claim 7, wherein the restriction site is provided after the first 33 bases inclusive of the triplet of nucleotides provided in place of the natural polyhedrin ATG translation start codon.

10. A vector according to claim 7, wherein the restriction site is a BamHl site.

11. A process for the preparation of a product encoded by a foreign gene, which process comprises culturing cells susceptible to baculovirus infection which are infected with a recombinant baculovirus comprising the following elements operably linked 5' to 3';
    (I) a polyhedrin promoter;
    (II) in place of the natural ATG translation start codon for the polyhedrin coding sequence, another triplet of nucleotides;
    (III) the next 21 to 47 bases of the N-terminal region of the polyhedrin coding sequence, which are thereby retained but not capable of being translated;
    (IV) immediately thereafter, a foreign gene provided with a translation start codon.

12. A process according to claims 7 or 11, wherein there is a single base change in the third base of the natural ATG translation start codon for the polyhedrin gene.

13. A process according to claim 12, wherein the said ATG codon has been changed to ATC.

14. A process according to claims 7 or 11, wherein the foreign gene is a procaryotic gene.

15. A process according to claims 7 or 11, wherein the foreign gene is a eucaryotic gene.

16. A process according to claims 7 or 11, wherein the foreign gene is a gene encoding human gamma-interferon.

17. A process according to claims 7 or 11, wherein the foreign gene is a gene encoding immediate early protein of human cytomegalovirus.

18. A process according to claims 7 or 11, wherein the foreign gene encodes a chimaeric protein consisting essentially of
    (i) a N-terminal signal sequence of the precursor to the major merozoite surface antigen (PMMSA) of *P. falciparum*,
    (ii) optionally, at least one epitope of the circumsporozoite protein of *P. falciparun*, and
    (iii) a C-terminal fragment of the PMMSA of *P. falciparum* with or without the C-terminal anchor sequence.

19. A process according to claim 7, wherein the cells susceptible to baculovirus infection are cells of the *Spodoptera frugiperda* insect cell line.

20. A process according to claim 11, wherein the cells susceptible to baculovirus infection are cells of the *Spodoptera frugiperda* insect cell line.

21. A process according to claim 11, wherein the foreign gene is provided after the first 27 to 39 bases of the N-terminal region of the polyhedrin gene inclusive of the triplet of nucleotides provided in place of the natural polyhedrin ATG translation start codon.

22. A vector according to claim 21, wherein the foreign gene is provided after the first 33 bases inclusive of the triplet of nucleotides provided in place of the natural polyhedrin ATG translation start codon.

* * * * *